US006077502A

United States Patent [19]
Witt et al.

[11] Patent Number: 6,077,502
[45] Date of Patent: Jun. 20, 2000

[54] ORAL CARE COMPOSITIONS COMPRISING CHLORITE AND METHODS

[75] Inventors: Jonathan James Witt, Cincinnati; Rohan Lalith Wimalasena, Liberty Township; Andrew Lee Wong; Eric Altman Goulbourne, Jr., both of West Chester, all of Ohio

[73] Assignee: The Procter & Gamble Company, Cincinnati, Ohio

[21] Appl. No.: 09/032,238

[22] Filed: Feb. 27, 1998

[51] Int. Cl.[7] .......................... A61K 7/20; A61K 33/20; A61K 9/20

[52] U.S. Cl. .......................... 424/53; 424/49; 424/464; 424/613; 424/661

[58] Field of Search .......................... 424/49–88

[56] References Cited

U.S. PATENT DOCUMENTS

| | | | |
|---|---|---|---|
| 3,271,242 | 9/1966 | McNicholas et al. | 167/17 |
| 3,278,447 | 10/1966 | McNicholas | 252/187 |
| 4,060,600 | 11/1977 | Vit | 424/53 |
| 4,084,747 | 4/1978 | Alliger | 239/4 |
| 4,139,589 | 2/1979 | Beringer et al. | 424/40 |
| 4,330,531 | 5/1982 | Alliger | 424/149 |
| 4,574,084 | 3/1986 | Berger | 424/128 |
| 4,585,482 | 4/1986 | Tice et al. | 106/15.05 |
| 4,592,487 | 6/1986 | Simon et al. | 222/94 |
| 4,656,039 | 4/1987 | Weiss et al. | 426/5 |
| 4,689,215 | 8/1987 | Ratcliff | 424/53 |
| 4,696,811 | 9/1987 | Ratcliff | 424/53 |
| 4,786,492 | 11/1988 | Ratcliff | 424/53 |
| 4,788,053 | 11/1988 | Ratcliff | 424/53 |
| 4,792,442 | 12/1988 | Ratcliff | 424/53 |
| 4,793,989 | 12/1988 | Ratcliff | 424/53 |
| 4,808,389 | 2/1989 | Ratcliff | 424/53 |
| 4,818,519 | 4/1989 | Ratcliff | 424/53 |
| 4,829,129 | 5/1989 | Kelley | 525/326.9 |
| 4,837,009 | 6/1989 | Ratcliff | 424/53 |
| 4,847,090 | 7/1989 | Della Posta et al. | 426/5 |
| 4,851,213 | 7/1989 | Ratcliff | 424/53 |
| 4,855,135 | 8/1989 | Ratcliff | 424/127 |
| 4,880,638 | 11/1989 | Gordon | 424/662 |
| 4,886,657 | 12/1989 | Ratcliff | 415/53 |
| 4,889,714 | 12/1989 | Ratcliff | 424/53 |
| 4,891,216 | 1/1990 | Kross et al. | 424/78 |
| 4,902,498 | 2/1990 | Agricola et al. | 424/52 |
| 4,925,656 | 5/1990 | Ratcliff | 424/53 |
| 4,971,806 | 11/1990 | Cherukuri et al. | 426/5 |
| 4,975,285 | 12/1990 | Ratcliff | 424/661 |
| 4,978,535 | 12/1990 | Ratcliff | 424/661 |
| 4,986,990 | 1/1991 | Davidson et al. | 424/665 |
| 5,019,402 | 5/1991 | Kross et al. | 424/665 |
| 5,052,590 | 10/1991 | Ratcliff | 222/94 |
| 5,100,652 | 3/1992 | Kross et al. | 424/53 |
| 5,185,161 | 2/1993 | Davidson et al. | 424/665 |
| 5,200,171 | 4/1993 | Ratcliff | 424/53 |
| 5,281,412 | 1/1994 | Lukacovic et al. | 424/52 |
| 5,348,734 | 9/1994 | Ratcliff | 424/53 |
| 5,437,879 | 8/1995 | Kabse et al. | 426/5 |
| 5,489,435 | 2/1996 | Ratcliff | 424/422 |
| 5,618,550 | 4/1997 | Ratcliff | 424/422 |
| 5,631,300 | 5/1997 | Wellinghoff | 514/772.3 |
| 5,650,446 | 7/1997 | Wellinghoff et al. | 514/772.3 |
| 5,738,840 | 4/1998 | Richter | 424/53 |
| 5,772,986 | 6/1998 | Kross | 424/53 |
| 5,820,822 | 10/1998 | Kross | 422/37 |

FOREIGN PATENT DOCUMENTS

| | | | |
|---|---|---|---|
| 0287074 | 10/1988 | European Pat. Off. | A01N 25/24 |
| 0565134A1 | 10/1993 | European Pat. Off. | A61K 33/20 |
| 2329753 | 12/1973 | Germany . | |
| 60-054311 | 3/1985 | Japan | A61K 7/16 |
| 60-105610 | 6/1985 | Japan | A61K 7/16 |
| 2104509A | 4/1990 | Japan | A01N 59/08 |
| 9-183706 | 7/1997 | Japan | A01N 59/08 |
| 10-248911 | 9/1998 | Japan | A61L 9/01 |
| 2289841A | 12/1995 | United Kingdom | A61K 7/20 |
| 2290233A | 12/1995 | United Kingdom | A61K 7/20 |
| WO 89/03179 | 4/1989 | WIPO | A01N 59/08 |
| WO 93/18781 | 9/1993 | WIPO | A61K 33/40 |
| WO 95/27472 | 10/1995 | WIPO | A61K 7/20 |
| WO 96/25916 | 8/1996 | WIPO | A61K 7/20 |
| WO 98/04235 | 2/1998 | WIPO | A61K 7/20 |

OTHER PUBLICATIONS

Technology Update (Advertisement) "Finally—A 'cure' for bad breath", *World Traveler*, p. 73, 1998.

Yates et al., "The Comparative Effect of Acidified Sodium Chlorite and Chlorhexidine Mouthrinses on Plaque Regrowth and Salivary Bacterial Counts", *J. Clin Periodontol*, vol. 24, pp. 603–609 (1997).

Richter, "Diagnosis and Treatment of Halitosis", *Compendium*, vol. 17, No. 4, pp. 370–384 (1996).

White et al., "Chemistry of Chlorites", *Industrial and Engineering Chemistry*, vol. 34, No. 7, pp. 782–792 (1942).

RetarDent Toothpaste box.

RetarDex Oral Rinse box.

RetaDex Oral Rinse bottle.

ProxiPure Fresh Breath Rinse bottle.

TheraBreath Power Drops bottle.

Breath Appeal Step 2 Activator Solution bottle.

Breath Appeal Step 1 Synergizer Solution bottle.

Breath Appeal Step 1 Synergizer Concentrate bottle.

TheraBreath Oral Rinse bottle.

(List continued on next page.)

*Primary Examiner*—Shep K. Rose
*Attorney, Agent, or Firm*—John M. Howell; Betty J. Zea; David L. Suter

[57] ABSTRACT

The present invention relates to oral care compositions, including therapeutic rinses, especially mouth rinses, as well as toothpastes, gels, tooth powders, chewing gums, mouth sprays, and lozenges (including breath mints), comprising at least a minimally effective amount of chlorite ion, wherein preferably the pH of the final composition is greater than 7 and level of chlorine dioxide or chlorous acid is less than about 50 ppm, preferably is essentially free of chlorine dioxide or chlorous acid. This invention further relates to a method for treating or preventing gingivitis, plaque, periodontal disease, and/or breath malodor, and/or for the whitening of teeth, in humans or other animals, by applying a safe and effective amount of the chlorite ion composition to the oral cavity.

16 Claims, No Drawings

OTHER PUBLICATIONS

TheraBreath Breath Spray bottle.
TheraBreath Tooth Gel bottle.
Profresh Chlorine Dioxide Deodorant Mouth Rinse bottle.
ProFresh Chlorine Dioxide Starter Rinse bottle.
Oxyfresh Toothpaste tube.
Oxyfresh Mint Mouthrinse bottle.
Rapid White Tooth Whitening System box.
U.S. application No. 09/032,234, Witt et al., filed Feb. 27, 1998.
U.S. application No. 09/032,237, Witt et al., filed Feb. 27, 1998.

ORAL CARE COMPOSITIONS COMPRISING CHLORITE AND METHODS

TECHNICAL FIELD

The present invention relates to oral care compositions, including therapeutic rinses, especially mouth rinses, as well as toothpastes, tooth gels, tooth powders, chewing gums, mouth sprays, and lozenges (including breath mints), comprising an effective amount of chlorite ion. This invention further relates to a method for treating or preventing conditions of the oral cavity, such as gingivitis, plaque, periodontal disease, and/or breath malodor, as well as to a method for whitening teeth, in humans or other animals.

BACKGROUND ART

Oral malodor, plaque, gingivitis, periodontal disease, and discoloration of the teeth, are all undesirable conditions that affect many people. First malodor of the oral cavity is also known as halitosis or bad breath. It is broadly estimated in the U.S. that 20–90 million individuals have oral malodor. It is generally believed that the cause of this condition is due to the presence of anaerobic bacteria, especially gram-negative anaerobic bacteria, in the mouth. These bacteria will generate volatile sulfur compounds (VSC) which are known to cause breath malodor.

It is recognized in the art that some breath malodor is caused by three chemical compounds. Specifically, these compounds are hydrogen sulfide (H—S—H), methyl mercaptan ($CH_3$—S—H) and dimethyl sulfide ($CH_2$—S—$CH_3$). These compounds result from the degradation of epithelial cells and bacteria in the oral cavity. Specifically, the polypeptide chains of the epithelial cell walls, are composed of a series of amino acids including cysteine and methionine which contain sulfur side chains. The death of microorganisms or epithelial cells results in degradation of the polypeptide chains into their amino acid components, especially cysteine and methionine. Cysteine and methionine are precursors to the formation of VSC.

It is also recognized in the art that oral malodor not only comes from the posterior dorsal surface of the tongue but also from periodontal pockets. Furthermore, a person with gingivitis or periodontal disease may have increased oral malodor from disintegrated epithelial cells. Epithelial cells turn over faster if inflammation is present. Therefore, a larger number of these dead epithelial cells remain in the oral cavity and will degrade into the malodorous compounds.

In addition VSC will also alter the epithelial barrier, permitting penetration of the barrier by antigenic substances. For example, VSC such as hydrogen sulfide, methyl mercaptan and dimethyl sulfide contribute to the penetration of bacterial toxins through the epithelial barrier into the underlying basal lamina and connective tissue. A. Rizzo, *Peridontics,* 5: 233–236 (1967); W. Ng and J. Tonzetich, *J. Dental Research,* 63(7): 994–997 (1984); M. C. Solis-Gaffar, T. J. Fischer and A. Gaffar, *J. Soc. Cosmetic Chem.,* 30: 241–247 (1979). Thereafter, bacterial toxins, bacteria and virus can invade the underlying gingival tissue adjacent to the sulcular space, thereafter invading the underlying connective tissue. A decrease in VSC will decrease the tissue permeability to oral toxins and bacteria.

Systemic entities can contribute to oral malodor as well. These entities include oral carcinomas, diabetes, liver and kidney abnormalities, medications which change the oral environment, ENT problems such as chronic sinusitis, tonsillitis and inflamed adenoids. Gastrointestinal problems do not contribute to chronic oral malodor, although this is a common belief Evaluation and diagnosis of oral malodor can be achieved with the Halimeter (Interscan). The Halimeter is a gas-analysis sensor that measures the volatile sulfur compounds in breath.

Furthermore, periodontal disease is also an undesirable condition which has widespread occurrence. Periodontal disease is a major cause of tooth loss in adults, beginning as early as age 12. Even by age 15, it is possible that 4 out of 5 persons already have gingivitis and possibly as many as 4 out of 10 have periodontitis.

Periodontal disease affects the periodontum, which is the investing and supporting tissues surrounding a tooth (i.e., the periodontal ligament, the gingiva, and the alveolar bone). Gingivitis and periodontitis are inflammatory disorders of the gingiva and the deeper periodontal tissues, respectively.

It is well accepted that periodontal disease is associated with the accumulation of plaque on the teeth. The teeth are coated with a salivary proteanaceous material (pellicle) and thereafter streptococci adhere to this coating. Gingivitis occurs from the dental plaque, and periodontitis is caused by the infection spreading to the periodontal pocket or space between the gingiva and the tooth root.

Furthermore, consumers are very interested in making their teeth whiter. Consumers consider people with whiter teeth as having more personal confidence and better social acceptance.

Teeth comprise both an inner dentin layer and an outer hard enamel layer. The enamel layer protects the inner dentin layer and live tissue and serves as the contact surface for mastication of solid food. The enamel layer is generally translucent and slightly off-white in color. It is also considered porous since the hydroxy apatite crystals that comprise the enamel form microscopic hexagonal rods or prisms having microscopic pores or channels between them. As a result of this porous structure, staining agents and discoloring substances, such as antibiotics, foods containing coloring materials, coffee, cola, tea, tabacco, etc., can permeate the enamel and change its surface to appear yellow or brownish in color.

While good oral hygiene, as achieved by brushing the teeth with a cleansing dentifrice, may help reduce the incidence of stain, gingivitis, plaque, periodontal disease, and/or breath malodor, it does not necessarily prevent or eliminate their occurrence. Microorganisms contribute to both the initiation and progression of gingivitis, plaque, periodontal disease, and/or breath malodor. Thus, in order to prevent or treat these conditions, these microorganisms must be suppressed by some means other than simple mechanical scrubbing. In addition, simple mechanical scrubbing will not be entirely effective to remove all stain types and/or whiten the teeth.

Towards this end, a great deal of research has been aimed at developing therapeutic compositions and methods of treating the above conditions, that are effective in suppressing microorganisms. Also, research has been aimed at developing effective whitening compositions. Some of this research has focused on oral care compositions and methods comprising chlorine dioxide or chlorine dioxide generating compounds. Chlorine dioxide is a very strong oxidant and is known as a broad spectrum antimicrobial agent.

The prior art discloses compositions and methods that use chlorine dioxide for the treatment of various oral care conditions. Most of these prior art references teach that the delivery of chlorine dioxide is essential to provide efficacy.

This is in contrast to the present invention which focuses on the delivery of chlorite ion to the oral cavity, to provide efficacy. The compositions and methods of the present invention are specifically and intentionally designed to avoid or minimize the production of chlorine dioxide in the compositions.

The prior art teaches a variety of ways to deliver chlorine dioxide, in oral care compositions, to the oral cavity. For example, U.S. Pat. Nos. 4,689,215 issued Aug. 25, 1987; 4,837,009 issued Jun. 6, 1989; 4,696,811, issued Sep. 29, 1987; 4,808,389 issued Feb. 28, 1989; 4,786,492 issued Nov. 22, 1988; 4,788,053 issued Nov. 29, 1988; 4,792,442 issued Dec. 20, 1988; 4,818,519 issued Apr. 4, 1989; 4,851, 21 issued Jul. 25, 1989; 4,855,135 issued Aug. 8, 1989; 4,793,989 issued Dec. 27, 1988; 4,886,657 issued Dec. 12, 1989; 4,889,714 issued Dec. 26, 1989; 4,925,656 issued May 15, 1990; 4,975,285 issued Dec. 4, 1990; 4,978,535 issued Dec. 18, 1990; 5,200,171 issued Apr. 6, 1993; 5,348, 734 issued Sep. 20, 1994; 5,618,550 issued Apr. 8, 1997, and 5,489,435 issued Feb. 6, 1996, all to Perry A. Ratcliffe, teach oral care compositions and methods of treatment using stabilized chlorine dioxide.

Additional prior art references, which teach the generation and delivery of chlorine dioxide with activator compounds such as protic acids, reducing sugar activators, etc., include: U.S. Pat. Nos. 5,281,412, Lukacovic et al., issued Jan. 25, 1994, The Procter & Gamble Co.; 5,110,652, Kross et al., issued Mar. 31, 1992, Alcide Corporation; 5,019,402, Kross et al., issued May 28, 1991, Alcide; 4,986,990, Davidson et al., issued Jan. 22, 1991, Alcide; 4,891,216, Kross et al., issued Jan. 2, 1990, Alcide; 4,330,531, Alliger, issued May 18, 1982; DE 2,329,753, published Dec. 13, 1973, National Patent Development Corp.; EP 287,074, Kross et al., published Oct. 19, 1988, Alcide; EP 565,134, Kross et al., published Oct. 13, 1993, Alcide; and WO/95/ 27472, Richter, published Oct. 19, 1995.

Additional prior art references relating to chlorine dioxide compositions include: GB 2,289,841, Mehmet, published Jun. 12, 1995, Janina International; GB 2,290,233, Drayson et al., published Dec. 20, 1995, Medical Express Limited; WO 96/25916, Van Den Bosch et al., published Aug. 29, 1996, Diamond White; JP 054,311, Tsuchikura, published Mar. 28, 1985; JP 105,610, Tsuchikura, published Jun. 11, 1985; and WO/89/03179, Partlow et al., published Apr. 20, 1989, New Generation Products. All of the above references are incorporated herein by reference in their entirety.

The above prior art references have not recognized that the delivery of chlorite ion, itself, to the oral cavity will provide efficacy in various oral care conditions. Because prior art references have focused on the delivery of chlorine dioxide for efficacy, prior art compositions and methods of treatment may have various drawbacks. For example, compositions comprising chlorine dioxide can exhibit aesthetic disadvantages such as "chlorine" (e.g. swimming pool) taste and smell. In addition due to the strong oxidizing capability of chlorine dioxide, compositions comprising chlorine dioxide may have certain stability disadvantages, especially in oral care formulations.

Therefore, prior art compositions, mentioned above, have not been entirely satisfactory for the treatment and/or prevention of gingivitis, plaque, periodontal disease, and/or breath malodor or for the whitening of teeth. Therefore, additional efficacious compositions and methods of treatment for these purposes are desirable.

As mentioned above, the present invention relates to the delivery of chlorite ion to the oral cavity for efficacy. The present invention is specifically designed to avoid or minimize the production of chlorine dioxide or chlorous acid in the compositions. The present invention, therefore, relates to oral care compositions comprising chlorite ion wherein no (or only very low levels of) chlorine dioxide or chlorous acid is generated or is present in the oral care compositions at the time of use. Moreover, the present invention preferably relates to oral care compositions comprising chlorite ion with relatively alkaline pHs, e.g. at pHs above 7, whereby no (or only very low levels of) chlorine dioxide or chlorous acid is generated or is present in the oral care composition at the time of use. Further, compositions of the present invention comprise at least a minimum amount of chlorite ion for effectiveness. These compositions and methods (of the present invention) are effective even though no (or only very low levels of) chlorine dioxide or chlorous acid is generated or is present in these compositions.

It is the purpose of the present invention to provide compositions and methods for treating or preventing diseases of the oral cavity, such as plaque, gingivitis, periodontal disease, and for treating or preventing other conditions such as breath malodor, in humans or other animals, by utilizing an effective amount of chlorite ion wherein no (or only very low levels of) chlorine dioxide or chlorous acid is generated or is present in the oral care composition at the time of use. The pH of the final composition is preferably alkaline, e.g. above pH 7.

It is also the purpose of the present invention to provide compositions and methods to whiten teeth, in humans or other animals, by utilizing an effective amount of chlorite ion wherein no (or only very low levels of) chlorine dioxide or chlorous acid is generated or is present in the oral care composition at the time of use. The pH of the final composition is preferably alkaline, e.g. above pH 7.

Further, the present invention relates to oral care compositions, including therapeutic rinses, especially mouth rinses, as well as toothpastes, tooth gels, tooth powders, non-abrasive gels, chewing gums, mouth sprays, and lozenges (including breath mints). These compositions comprise a minimally effective amount of chlorite ion.

These compositions are effective in killing, and/or altering the bacterial metabolism, and/or for a period of time suppressing the growth of, microorganisms which cause topically-treatable infections and diseases of the oral cavity, such as plaque, gingivitis, periodontal disease, and breath malodor. These compositions are also effective to whiten teeth.

SUMMARY OF THE INVENTION

The present invention relates to oral care compositions, including therapeutic rinses, especially mouth rinses, as well as toothpastes, tooth gels, tooth powders, non-abrasive gels, chewing gums, mouth sprays, and lozenges (including breath mints), comprising:

(a) a safe and effective amount, preferably a minimally effective amount, of chlorite ion; and (b) a pharmaceutically-acceptable topical, oral carrier; wherein the level of chlorine dioxide or chlorous acid in the final composition is less than about 50 ppm; and preferably the pH of the final composition is greater than 7. More preferably the pH of the composition is greater than 7.6, even more preferably greater than 8.

This invention further relates to a method for treating or preventing diseases of the oral cavity, such as gingivitis, plaque, periodontal disease, and/or breath malodor, and/or for the whitening of teeth, in humans or other animals, by applying the above compositions to the oral cavity and/or teeth.

DETAILED DESCRIPTION OF THE INVENTION

The present invention relates to compositions and methods of treating or preventing diseases of the oral cavity (e.g. plaque, gingivitis, periodontal disease), breath malodor, and for whitening teeth, in humans or other animals, by topically applying to the oral cavity, a safe and effective amount of chlorite ion.

By "diseases or conditions of the oral cavity," as used herein, is meant diseases of the oral cavity including periodontal disease, gingivitis, periodontitis, periodontosis, adult and juvenile periodontitis, and other inflammatory conditions of the tissues within the oral cavity, plus caries, necrotizing ulcerative gingivitis, and other conditions such as oral or breath malodor. Also specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, Anaerobic Bacteria in Human Diseases, chapter 4, pp 78–104, and chapter 6, pp 115–154 (Academic Press, Inc., NY, 1977), the disclosures of which are incorporated herein by reference in their entirety. The compositions and methods of treatment of the present invention are particularly effective for treating or preventing periodontal disease (gingivitis and/or periodontitis) and breath malodor.

By "safe and effective amount" as used herein is meant an amount of a chlorite ion, high enough to significantly (positively) modify the condition to be treated or to effect the desired whitening result, but low enough to avoid serious side effects (at a reasonable benefit/risk ratio), within the scope of sound medical/dental judgment. The safe and effective amount of a chlorite ion, will vary with the particular condition (e.g., to effect whitening, to treat disease of the oral cavity or malodor) being treated, the age and physical condition of the patient being treated, the severity of the condition, the duration of treatment, the nature of concurrent therapy, the specific form (i.e., salt) of the chlorite source employed, and the particular vehicle from which the chlorite ion is applied.

By "toothpaste" as used herein is meant paste, powder, and tooth gel formulations unless otherwise specified.

By "oral care composition" or "oral composition" as used herein is meant a product which is not intentionally swallowed for purposes of systemic administration of therapeutic agents, but is retained in the oral cavity for a sufficient time to contact substantially all of the dental surfaces and/or oral mucosal tissues for purposes of oral activity.

By "essentially free of chlorous acid or chlorine dioxide" as used herein is meant a composition which comprises very low levels, e.g. less than about 5 ppm, preferably less than about 1 ppm of chlorine dioxide or chlorous acid, using known analytical methods for measuring chlorine dioxide or chlorous acid as disclosed hereinafter.

Chlorite Ion Source

The present invention includes chlorite ion as an essential ingredient in the compositions and methods of the present invention. The chlorite ion can come from any type of chlorite salt. Examples include alkali metal chlorites, alkaline earth metal chlorites, and any other transition metals, inner transition metal chlorites and/or polymeric salts. Water soluble chlorite salts are preferred. Examples of suitable metal chlorites include calcium chlorite, barium chlorite, magnesium chlorite, lithium chlorite, sodium chlorite and potassium chlorite. Sodium chlorite and potassium chlorite are preferred. Sodium chlorite is particularly preferred. Mixtures of two or more sources of chlorite may also be used.

While not intending to be bound by theory, the present inventors believe that chlorite ion provides antimicrobial activity, especially selectivity for gram negative anaerobes, for oral care compositions.

For dentifrice compositions of the present invention, the level of chlorite ion is greater than about 0.02%, preferably greater than about 0.4%, more preferably greater than about 0.56%, even more preferably greater than about 0.75%, and even more preferably greater than about 1%, by weight of the composition. The composition preferably comprises about 2% by weight of the composition, of chlorite ion.

For mouthrinse compositions of the present invention, the level of chlorite ion is greater than about 0.04%, preferably greater than about 0.075%, more preferably greater than about 0.15%, by weight of the composition.

For lozenge or breath mint compositions of the present invention, the amount of chlorite ion is from about 0.1 mg to about 12 mg, preferably from about 1 mg to about 6 mg, per unit.

For gum compositions of the present invention, the amount of chlorite ion is from about 0.1 mg to about 12 mg, preferably from about 1 mg to about 6 mg, per unit.

For methods of treating or preventing gingivitis or for whitening the teeth, preferably the compositions comprise from about 0.75% to about 6%, of chlorite ion, by weight of the composition.

In the context of breath odor elimination or reduction, the compositions and methods of the present invention provide long-lasting breath protection, e.g. greater than about 3 hours.

For methods of treating or preventing oral malodor, and for breath protection lasting greater than about 3 hours, preferably the compositions comprise from about 0.04% to about 6%, of chlorite ion, by weight of the composition.

Chlorite salts are available from various suppliers as sodium chlorite. Sodium chlorite is commercially available as a technical grade powder or flake, and as an aqueous liquid concentrate in a range of concentrations. Example of sources of sodium chlorite include: sodium chlorite available from Aragonesas and from Vulcan. These sources generally have no more than 4% sodium chlorate as well. Preferably the ratio of chlorite to chlorate is greater than 8:1 and generally about 20:1.

Preferably, the source of chlorite ion has high purity, e.g. 70% or greater. Furthermore, preferably the compositions of the present invention are essentially free of hypochlorite metal salt or hypochlorite ion, dichloroisocyanurate, or salts thereof.

Preferably, the level of chlorite ion is measured by gradient separation of inorganic and organic acid anions using Ion Pac ASII exchange column, available from Dionex Corporation, Sunnyvale, Calif.

The final compositions of the present invention preferably comprise low levels of chlorine dioxide or chlorous acid, or are essentially free of chlorine dioxide or chlorous acid (have less than about 5 ppm, preferably less than about 1 ppm of chlorine dioxide or chlorous acid).

For mouthwash and dentifrice compositions the level of chlorine dioxide or chlorous acid in the final composition is preferably less than about 50 ppm, more preferably less than about 25 ppm, and even more preferably less than about 10 ppm.

For dual phase compositions the level of chlorine dioxide or chlorous acid is measured within about 2 to 3 minutes after the two phases are mixed together.

Analytical methods to measure the levels of chlorine dioxide or chlorous acid in the compositions of the present invention are known in the art. For example, L. S. Clesceri, A. E. Greenberg, and R. R. Trussel, *Standard Methods for the Examination of Water and Wastewater,* $17^{th}$ ed., American Public Health Association, Washington, D.C., 1989, pp. 4–75 through 4–83; E. M. Aieta, P. V. Roberts, and M. Hernandez, *J.Am. Water Works Assoc.* 76(1), pp. 64–70 (1984); J. D. Pfaff and C. A. Brockhoff, *J. Am. Water Works Assoc.* 82(4), pp. 192–195 (1990); G. Gordon, W. J. Cooper, R. G. Rice, and G. E. Pacey, *J. Am. Water Works Assoc.* 80(9), pp. 94–108 (1988); D. L. Harp, R. L. Klein, and D. J. Schoonover, *J. Am. Water Works Assoc.* 73(7), pp. 387–389 (1981); G. Gordon, W. J. Cooper, R. G. Rice, and G. E. Pacey, Am. Water Works Assoc. Res. Foundation, Denver, Colo., 1987, pp. 815. All of these references are herein incorporated by reference in their entirety.

The pH of the final composition (either a single phase or dual phase composition) of the present invention is greater than 7, preferably greater than 7.6, more preferably greater than 8. Preferably the pH of the final composition is from 8 to 12, more preferably the pH is 10.

Preferably for mouthwash compositions the pH of the final composition is greater than 7.5, preferably greater than 8. Preferably the pH of the final composition is from 8 to 12, more preferably the pH is 10.

Preferably for dentifrice compositions the pH of the final composition is greater than 7.6, preferably greater than 8, more preferably greater than 9. Preferably the pH of the final composition is from 8 to 12, more preferably the pH is 10.

For dual phase compositions the pH is measured after the two phases are mixed together, and is not based on the pH of a single phase prior to mixing.

The pH of the final dentifrice composition is measured from a 3:1 aqueous slurry of toothpaste, e.g. 3 parts water to 1 part toothpaste.

Pharmaceutically-Acceptable Excipients

By "pharmaceutically-acceptable excipient" or "pharmaceutically-acceptable oral carrier," as used herein, is meant one or more compatible solid or liquid filler diluents or encapsulating substances which are suitable for topical, oral administration. By "compatible," as used herein, is meant that the components of the composition are capable of being commingled without interaction in a manner which would substantially reduce the composition's stability and/or efficacy for treating or preventing breath malodor, plaque, gingivitis, periodontal disease and to whiten the teeth, according to the compositions and methods of the present invention.

The carriers or excipients of the present invention can include the usual and conventional components of toothpastes (including gels and gels for subgingival application), mouth rinses, mouth sprays, chewing gums, and lozenges (including breath mints) as more fully described hereinafter.

The compositions of the present invention can be dual phase compositions or single phase compositions. The chlorite ion, however, is relatively reactive and will react with certain carriers or excipients generally used in oral care compositions. Therefore, based on this reactivity, the preferred compositions of the present invention are dual phase compositions. These compositions comprise a first phase and a second phase:

(a) the first phase comprising chlorite ion; and (b) the second phase comprising a pharmaceutically-acceptable topical, oral carrier and comprising no chlorite.

These dual phase compositions comprise two phases, wherein chlorite ion is placed in a first phase which is to be kept separate from the second phase. The first phase comprising chlorite ion can additionally comprise pharmaceutically-acceptable topical, oral carriers which are compatible with chlorite ion. Preferably the first phase, in addition to chlorite, comprises one (or more) compatible binder, humectant, buffer and/or preservative. Preferably, the second phase, which comprises no chlorite, comprises flavorant, surfactant, fluoride ion, and/or abrasive.

Normally, each phase in these two phase compositions, is in a separate container or in a single container with two chambers. Prior to use of dual phase composition by the consumer, the two phases are combined by coextrusion of the two separate phases, preferably at a 1:1 volume to volume ratio, and the composition is preferably used immediately after preparation, i.e. within about 5 minutes.

The two phases, however, can be combined from about 1 minute to about 1 hour before use, or during the use of the composition.

Dual phase containers are disclosed in U.S. Pat. Nos. 5,052,590, Ratcliffe, issued Oct. 1, 1991 and 4,330,531, Alliger, issued May 18, 1982.

In another preferred embodiment, chlorite is substantially anhydrous until just prior to use. For example, preparing a mouth rinse solution just prior to use by dissolving in water, a substantially anhydrous concentrate of chlorite, to the necessary concentration for use in the method of treatments of the present invention.

The choice of a carrier to be used is basically determined by the way the composition is to be introduced into the oral cavity. If a toothpaste (including tooth gels, etc.) is to be used, then a "toothpaste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al., which is incorporated herein by reference; if a chewing gum is to be used, then a "chewing gum carrier" is chosen, as disclosed in, e.g., U.S. Pat. No. 4,083,955, to Grabenstetter et al., which is incorporated herein by reference (e.g., gum base, flavoring and sweetening agents). If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. Nos. 5,198,220, Damani, issued Mar. 30, 1993, P&G, 5,242,910, Damani, issued Sep. 7, 1993, P&G, all of which are incorporated herein by reference. Carriers suitable for the preparation of compositions of the present invention are well known in the art. Their selection will depend on secondary considerations like taste, cost, and shelf stability, etc.

Preferred compositions of the subject invention are in the form of dentifrices, such as toothpastes, tooth gels and tooth powders. Components of such toothpaste and tooth gels generally include one or more of a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the present invention are non-abrasive gels, including subgingival gels, which generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), water (from about 2% to about 45%), and may comprise an anticaries agent (from about 0.05% to about 0.3% as fluoride ion), and an anticalculus agent (from about 0.1% to about 13%).

Other preferred compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred compositions of the subject invention are dental solutions. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and fast-dissolving solid forms including compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in copending U.S. patent application Ser. No. 08/253,890, filed Jun. 3, 1994, Brideau; U.S. Pat. 4,642,903; U.S. Pat. No. 4,946,684; U.S. Pat. No. 4,305,502; U.S. Pat. No. 4,371,516; U.S. Pat. No. 5,188,825; U.S. Pat. No. 5,215,756; U.S. Pat. No. 5,298,261; U.S. Pat. No. 3,882,228; U.S. Pat. No. 4,687,662; U.S. Pat. No. 4,642,903. All of these patents are incorporated herein by reference in their entirety.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: The Science and Practice of Pharmacy, $19^{th}$ Ed., Vol. II, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994, which is herein incorporated by reference in its entirety.

The compositions of the present invention are preferably essentially free of organic solvents. The compositions of the present invention are also preferably essentially free of peroxy compounds.

Types of carriers or oral care excipients which may be included in compositions of the present invention, along with specific non-limiting examples, are:

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, Zeodent®, particularly the silica carrying the designation Zeodent 119®. The types of silica dental abrasives useful in the toothpastes of the present invention are described in more detail in Wason, U.S. Pat. No. 4,340,583, issued Jul. 29, 1982. The abrasive in the toothpaste compositions described herein is generally present at a level of from about 6% to about 70% by weight of the composition. Preferably, toothpastes contain from about 10% to about 50% of abrasive, by weight of the composition.

A particularly preferred precipitated silica is the silica disclosed in U.S. Pat. Nos. 5,603,920, issued on Feb. 18, 1997; 5,589,160, issued Dec. 31, 1996; 5,658,553, issued Aug. 19, 1997; 5,651,958, issued Jul. 29, 1997, all of which are assigned to the Procter & Gamble Co. All of these patents are incorporated herein by reference in their entirety.

Mixtures of abrasives can be used. All of the above patents regarding dental abrasives are incorporated herein by reference. The total amount of abrasive in dentifrice compositions of the subject invention preferably range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Sudsing Agents (Surfactants)

Suitable sudsing agents are those which are reasonably stable and form foam throughout a wide pH range. Sudsing agents include nonionic, anionic, amphoteric, cationic, zwitterionic, synthetic detergents, and mixtures thereof. Many suitable nonionic and amphoteric surfactants are disclosed by U.S. Pat. Nos. 3,988,433 to Benedict; U.S. Pat. No. 4,051,234, issued Sep. 27, 1977, and many suitable nonionic surfactants are disclosed by Agricola et al., U.S. Pat. No. 3,959,458, issued May 25, 1976, both incorporated herein in their entirety by reference.

a.) Nonionic and amphoteric surfactants

Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

The present composition can typically comprise a nonionic, amphoteric, or combination of nonionic and amphoteric surfactant each at a level of from about 0.025% to about 5%, preferably from about 0.05% to about 4%, and most preferably from about 0.1% to about 3%.

b.) Anionic surfactants

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. The present composition typically comprises an anionic surfactant at a level of from about 0.025% to about 9%, preferably from about 0.05% to about 7%, and most preferably from about 0.1% to about 5%.

Fluoride Ions

The present invention may also incorporate free fluoride ions. Preferred free fluoride ions can be provided by sodium fluoride, stannous fluoride, indium fluoride, and sodium monofluorophosphate. Sodium fluoride is the most preferred free fluoride ion. Norris et al., U.S. Pat. No. 2,946,725, issued Jul. 26, 1960, and Widder et al., U.S. Pat. No. 3,678,154 issued Jul. 18, 1972, disclose such salts as well as others. These patents are incorporated herein by reference in their entirety.

The present composition may contain from about 50 ppm to about 3500 ppm, and preferably from about 500 ppm to about 3000 ppm of free fluoride ions.

Thickening Agents

In preparing toothpaste or gels, it is necessary to add some thickening material to provide a desirable consistency of the composition, to provide desirable chlorite release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Some thickening agents, however, except polymeric polyether compounds, e.g., polyethylene or polypropylene oxide (M.W. 300 to 1,000,000), capped with alkyl or acyl groups containing 1 to about 18 carbon atoms, may react with chlorite. When chlorite is formulated separately in a dual phase composition, preferred thickening agents are hydroxyethyl cellulose and water-soluble salts of cellulose ethers such as sodium carboxymethyl cellulose and sodium carboxymethyl hydroxyethyl cellulose.

A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220, Damani, issued Mar. 30, 1993, P&G, 5,242,910, Damani, issued Sep. 7, 1993, P&G, and 4,443,430, Mattei, issued Apr. 17, 1984, all of which are incorporated herein by reference.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3–1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety.

Preferred salivating agents of the present invention include Jambus® manufactured by Takasago. Preferred warming agents include capsicum and nicotinate esters, such as benzyl nicotinate. Preferred numbing agents include benzocaine, lidocaine, clove bud oil, and ethanol.

Anticalculus Agent

The present invention also includes an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology,* Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutaric acids), and mixtures thereof.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 5% to about 70%, and preferably from about 20% to about 50%, by weight of the composition herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

Antimicrobial antiplaque agents can also by optionally present in oral compositions. Such agents may include, but are not limited to, triclosan, 5-chloro-2-(2,4-dichlorophenoxy)-phenol, as described in *The Merck Index* 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (*Merck Index*, no. 2090), alexidine (*Merck Index*, no. 222; hexetidine (*Merck Index*, no. 4624); sanguinarine (*Merck Index*, no. 8320); benzalkonium chloride (*Merck Index*, no. 1066); salicylanilide (*Merck Index*, no. 8299); domiphen bromide (*Merck Index*, no. 3411); cetylpyridinium chloride (CPC) (*Merck Index*, no. 2024; tetradecylpyridinium chloride (TPC); N-tetradecyl4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above antimicrobial antiplaque agents. If present, the antimicrobial antiplaque agents generally comprise from about 0.1% to about 5% by weight of the compositions of the present invention.

Anti-inflammatory agents may also be present in the oral compositions of the present invention. Such agents may include, but are not limited to, non-steroidal anti-inflammatory agents such as aspirin, ketorolac, flurbiprofen, ibuprofen, naproxen, indomethacin, aspirin, ketoprofen, piroxicam and meclofenamic acid, and mixtures thereof. If present, the anti-inflammatory agents generally comprise from about 0.001% to about 5% by weight of the compositions of the present invention. Ketorolac is described in U.S. Pat. No. 5,626,838, issued May 6, 1997. Both of these references are incorporated herein by reference in their entirety.

Other optional agents include synthetic anionic polymeric polycarboxylates being employed in the form of their free acids or partially or preferably fully neutralized water soluble alkali metal (e.g. potassium and preferably sodium) or ammonium salts and are disclosed in U.S. Pat. No. 4,152,420 to Gaffar, U.S. Pat. No. 3,956,480 to Dichter et al., U.S. Pat. No. 4,138,477 to Gaffar, U.S. Pat. No. 4,183,914 to Gaffar et al., and U.S. Pat. No. 4,906,456 to Gaffar et al. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139 (M.W. 500,000), A.N. 119 (M.W. 250,000) and preferably S-97 Pharmaceutical Grade (M.W. 70,000), of GAF Corporation.

The present invention can also optionally comprise selective H-2 antagonists including compounds disclosed in U.S. Pat. No. 5,294,433, Singer et al., issued Mar. 15, 1994, which is herein incorporated by reference in its entirety.

Composition Use

A safe and effective amount of the compositions of the present invention and/or chlorite ion may be topically applied to the mucosal tissue of the oral cavity, to the gingival tissue of the oral cavity, and/or to the surface of the teeth, for the treatment or prevention of the above mentioned diseases or conditions of the oral cavity,. in several conventional ways. For example, the gingival or mucosal tissue may be rinsed with a solution (e.g., mouth rinse, mouth spray) containing chlorite ion; or if chlorite ion is included in a dentifrice (e.g., toothpaste, tooth gel or tooth powder), the gingival/mucosal tissue or teeth is bathed in the liquid and/or lather generated by brushing the teeth. Other non-limiting examples include applying a non-abrasive gel or paste, which contains chlorite ion, directly to the gingival/mucosal tissue or to the teeth with or without an oral care appliance described below; chewing gum that contains chlorite; chewing or sucking on a breath tablet or lozenge which contains chlorite ion. Preferred methods of applying chlorite ion to the gingival/mucosal tissue and/or the teeth are via rinsing with a mouth rinse solution and via brushing with a dentifrice. Other methods of topically applying chlorite ion to the gingival/mucosal tissue and the surfaces of the teeth are apparent to those skilled in the art.

The concentration of chlorite ion in the composition of the present invention depends on the type of composition (e.g., toothpaste, mouth rinse, lozenge, gum, etc.) used to apply the chlorite ion to the gingival/mucosal tissue and/or the teeth, due to differences in efficiency of the compositions contacting the tissue and teeth, and due also to the amount of the composition generally used. The concentration may also depend on the disease or condition being treated.

It is preferred that the mouth rinse to be taken into the oral cavity have a concentration of chlorite ion in the range of from about 0.04% to about 0.4%, with from about 0.075% to about 0.2% more preferred and from about 0.1% to about 0.2%, by weight of the composition, even more preferred. Preferably mouth rinse compositions of the present invention deliver 3.75 to 22.5 mg of chlorite ion to the oral cavity when approximately 15 ml of the rinse is used.

Mouth sprays preferably have chlorite ion concentrations from about 0.15% to about 4%, with from about 0.2% to about 4% more preferred, with from about 0.75% to about 2%, by weight of the composition, even more preferred.

Preferably for dentifrices (including toothpaste and tooth gels) and non-abrasive gels, the concentration of chlorite ion is in the range of from about 0.4% to about 4.5%, by weight of the composition, with from about 0.75% to about 3% preferred, and from about 1.5% to about 2%, by weight of the composition, even more preferred.

Chewing gums and lozenges (including breath mints), are generally formulated into compositions of individual unit size preferably containing from about 0.1 mg to about 12 mg, preferably from about 1 mg to about 6 mg, of chlorite ion, per unit used in the oral cavity (i.e. per stick of gum, lozenge, breath mint, etc.).

For dual phase compositions the above concentrations of chlorite ion represent the concentration of chlorite ion after the two phases are mixed together, which is usually just prior to use by the consumer.

For the method of treating diseases or conditions of the oral cavity, including breath malodor (as well as long lasting breath protection), of the present invention, a safe and effective amount of chlorite ion is preferably applied to the gingival/mucosal tissue and/or the teeth (for example, by rinsing with a mouthrinse, directly applying a non-abrasive gel with or without a device, applying a dentifrice or a tooth gel with a toothbrush, sucking or chewing a lozenge or breathmint, etc.) preferably for at least about 10 seconds, preferably from about 20 seconds to about 10 minutes, more preferably from about 30 seconds to about 60 seconds. The method often involves expectoration of most of the composition following such contact. The frequency of such contact is preferably from about once per week to about four times per day, more preferably from about thrice per week to about three times per day, even more preferably from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, such as with the treatment of periodontal disease, a mouthrinse can be delivered to the periodontal pocket using a syringe or water injection device. These devices are known to one skilled in the art. Devices of this type include "Water Pik" by Teledyne Corporation. After irrigating, the subject can swish the rinse in the mouth to also cover the dorsal tongue and other gingival and mucosal surfaces. In addition a toothpaste, non-abrasive gel, toothgel, etc. can be brushed onto the tongue surface and other gingival and mucosal tissues of the oral cavity.

For the method of whitening teeth of the oral cavity, a safe and effective amount of chlorite ion is preferably applied, with or without an oral care device such as a toothbrush, tray containing the composition, plastic strips (as disclosed hereinafter), etc., to the surface of the teeth: for mouthrinses or mouthsprays and for toothpastes or tooth gels, preferably for at least about 10 seconds, preferably from about 20 seconds to about 10 minutes, more preferably from about 30 seconds to about 60 seconds and for non-abrasive gels (applied with an appliance) preferably at least about 10 minutes to about 12 hours, preferably from about 20 seconds to about 10 minutes. The method often involves expectoration of most of the composition following such contact, preferably followed with rinsing, e.g. with water. The frequency of such contact is preferably from about once per week to about four times per day, more preferably from about thrice per week to about three times per day, even more preferably from about once per day to about twice per day. The period of such treatment typically ranges from about one day to a lifetime. The subject may repeat the application as needed to whiten their teeth. The duration of treatment is preferably from about 3 weeks to about 3 months, but may be shorter or longer depending on the severity of the tooth discoloration being treated, the particular delivery form utilized and the patient's response to treatment.

In a preferred application, the consumer applies to their teeth, a thin plastic film pre-coated with the present composition, and wears it from about 10 minutes to 8 hours as described above. The consumer uses a new strip for each application of the present composition. This type of strip appliance is further described in P&G Copending applications Ser. Nos. 08/870,664; 08/870,330; 08/870,331 and 08/870,665 all filed Jun. 6, 1997, the disclosures of which are herein incorporated by reference in their entirety.

The following non-limiting examples further describe preferred embodiments within the scope of the present invention. Many variations of these examples are possible without departing from the scope of the invention.

All percentages used herein are by weight of the composition unless otherwise indicated.

EXAMPLES

The following examples are made by conventional processes by mixing the following:

Example 1—Dual Phase Dentifrice

| Dentifrice Phase | | Chlorite Phase | |
|---|---|---|---|
| Ingredient | Wt. % | Ingredient | Wt % |
| Water | 20.680 | Sodium Chlorite (80%) | 7.50 |
| Sorbitol (70% Solution) | 18.534 | Carbopol 956[2] | 5.62 |
| Glycerin | 9.000 | Water | 83.14 |
| Sodium Carbonate | 1.000 | Sodium Carbonate | 0.53 |
| Sodium Fluoride | 0.486 | Sodium Bicarbonate | 0.42 |
| Propylene Glycol | 8.000 | Sodium Hydroxide | 2.79 |
| Hydrated Silica | 30.00 | | |
| Xanthan Gum | 0.500 | | |
| Carboxymethyl Cellulose[1] | 0.400 | | |
| Sodium alkyl sulfate (27.9% Sol'n) | 8.000 | | |
| Titanium Dioxide | | | |
| Sodium Saccharin | 0.700 | | |
| Flavor | 0.600 | | |
| Methyl Paraben | 2.000 | | |
| Propyl Paraben | 0.070 | | |
| | 0.030 | Chlorite phase pH = 10 | |
| Total | 100.00 | Total | 100.00 |

After phases mixed in a 1:1 vol./vol. ratio, pH approximately 8.5 to 9.
[1]Grade 7M8SF from Aqualon.
[2]Available from B. F. Goodrich.

Example 2—Dual Phase Dentifrice

| Dentifrice Phase | | Chlorite Phase | |
|---|---|---|---|
| Ingredient | Wt. % | Ingredient | Wt % |
| Water | 22.180 | Sodium Chlorite (80%) | 2.50 |
| Sorbitol (70% Solution) | 13.534 | Carbopol 956[2] | 3.72 |
| Glycerin | 9.000 | Water | 91.07 |
| Disodium Phosphate | 4.500 | Sodium Carbonate | 0.53 |
| Sodium Fluoride | 0.486 | Sodium Bicarbonate | 0.42 |
| Propylene Glycol | 8.000 | Sodium Hydroxide | 1.76 |
| Hydrated Silica | 30.00 | | |
| Xanthan Gum | 0.500 | | |
| Carboxymethyl Cellulose[1] | 0.400 | | |
| Sodium alkyl sulfate (27.9% Sol'n) | 8.000 | | |
| Titanium Dioxide | 0.700 | | |
| Sodium Saccharin | 0.600 | | |
| Flavor | 2.000 | | |
| Methyl Paraben | 0.070 | | |
| Propyl Paraben | 0.030 | | |
| | | Chlorite phase pH = 10 | |
| Total | 100.00 | Total | 100.00 |

After phases mixed in a 1:1 vol./vol. Ratio, pH approximately 7.5.
[1]Grade 7M8SF from Aqualon.
[2]Available from B. F. Goodrich.

Example 3—Single Phase Dentifrice

| Ingredient | Wt. % |
|---|---|
| Water | 62.277 |
| Sodium Chlorite | 3.750 |
| Sodium Fluoride | 0.243 |
| Hydrated Silica | 25.000 |
| Xanthan Gum | 0.600 |
| Carbomer 956[1] | 0.200 |
| Sodium alkyl sulfate (27.9% Sol'n) | 4.000 |
| Titanium Dioxide | 1.000 |
| Sodium Saccharin | 0.130 |
| Flavor | 1.000 |
| Sodium Hydroxide (50% Sol'n) | 1.800 |
| Total | 100.00 |

[1]Available from B. F. Goodrich.
pH approximately 10.

Example 4—Dual Phase Mouthwash

| Mouthwash Phase | | Chlorite Phase | |
|---|---|---|---|
| Ingredient | Wt. % | Ingredient | Wt. % |
| Water | 45.00 | Sodium Chlorite (80%) | 0.25 |
| Glycerin | 19.24 | Water | 98.80 |
| Sodium Bicarbonate | 1.00 | Sodium Carbonate | 0.53 |
| Poloxamer 407 | 0.80 | Sodium Bicarbonate | 0.42 |
| Polysorbate 80 | 0.20 | | |
| Sodium Saccharin | 0.20 | | |
| Flavor | 0.50 | | |
| Color | 0.06 | | |
| Alcohol | 33.00 | pH = 10 | |
| Total | 100.00 | Total | 100.00 |

Example 5—Single Phase Mouthwash

| Ingredient | Wt % |
|---|---|
| Water | 98.80 |
| Sodium Chlorite | 0.25 |
| Sodium Carbonate | 0.53 |
| Sodium Bicarbonate | 0.42 |
| Total | 100.00 |

Example 6—Chlorite Lozenge

| Ingredient | |
|---|---|
| Na Chlorite | 6 mg. Per lozenge |
| Flavor | As desired |
| Magnesium Stearate | 7.5 mg. |
| Stearic Acid | 75 mg. |
| Compressible Sugar | QS 1500 mg. |

Example 7

| Dry Powder Mouthrinse for Reconstitution | |
|---|---|
| Ingredient | Weight % |
| Spray Dried Ethanol[1] | 85.38 |
| Sodium Bicarbonate | 5.34 |
| Sodium Chlorite (80%) | 1.60 |
| Tastemaker Spray Dried Spearmint #214487 | 6.40 |
| Aspartame | 0.43 |
| Acesulfame Potassium | 0.85 |
| Total | 100.00 |

[1]30% load, available from Takasago.

Example 8

| Dry Powder Mouthrinse for Reconstitution | |
|---|---|
| Ingredient | Weight % |
| Spray Dried Ethanol[1] | 75.00 |
| Sodium Bicarbonate | 15.72 |
| Sodium Chlorite (80%) | 1.60 |
| Tastemaker Spray Dried Spearmint #214487 | 6.40 |
| Aspartame | 0.43 |
| Acesulfame Potassium | 0.85 |
| Total | 100.00 |

[1]30% load, available from Takasago.

Add dry ingredients, listed above, in any order, and mix until achieving a homogeneous mixture. Colorants, to provide color after adding water to the dry mixture, are optional.

To make finished mouthwash:

Example 7: Add 1.874 grams of dry powder blend to 15 ml. of $H_2O$ in a small dose cup with lid. Shake vigorously until solids dissolve, rinse and expectorate.

Example 8: Add 1.874 grams of dry powder blend to 15 ml. of $H_2O$ in small dose cup with lid. Shake vigorously until solids dissolve, rinse and expectorate.

Example 9

| Non-Abrasive Gel | |
|---|---|
| Ingredient | Weight % |
| Sodium Chlorite (80%) | 3.75 |
| Carbopol 956[1] | 8.00 |
| Sodium Bicarbonate | 0.84 |
| Sodium Hydroxide (50% Solution) | 8.00 (approx. sufficient to get pH 10) |
| Water | QS 100% |

[1]Available from B. F. Goodrich.

Example 10

| Non-Abrasive Gel | |
|---|---|
| Ingredient | Weight % |
| Sodium Chlorite (80%) | 3.18 |
| Carbopol 956[1] | 3.90 |
| Sodium Bicarbonate | 0.84 |
| Sodium Hydroxide (50% Solution) | 3.90 (approx. sufficient to get pH 10) |
| Water | QS 100% |

[1]Available from B. F. Goodrich.

For Examples 9 and 10, disperse the Carbopol in water. Thereafter, add the sodium hydroxide and mix. Then add the sodium bicarbonate and mix. Check the pH and adjust to pH of 10 with sodium hydroxide, if needed. Finally, add the sodium chlorite and mix.

What is claimed is:

1. An oral care lozenge composition consisting essentially of:

(a) from about 0.1 mg to about 12 mg of chlorite ion; and (b) a pharmaceutically-acceptable lozenge oral carrier; wherein the level of chlorine dioxide or chlorous acid in the final composition is less than about 50 ppm and the pH of the final composition is greater than 7.

2. The composition of claim 1 wherein the composition comprises from about 1 mg to about 6 mg of chlorite ion.

3. The composition of claim 1 wherein the level of chlorine dioxide or chlorous acid in the final composition is less than about 25 ppm.

4. The composition of claim 3 wherein the level of chlorine dioxide or chlorous acid in the final composition is less than about 15 ppm.

5. The composition of claim 4 wherein the level of chlorine dioxide or chlorous acid in the final composition is less than about 10 ppm.

6. The composition of claim 5 wherein the final composition is essentially free of chlorine dioxide or chlorous acid.

7. An oral care lozenge composition consisting essentially of:

(a) a safe and effective amount of chlorite ion; and (b) a pharmaceutically-acceptable lozenge oral carrier;

wherein the level of chlorine dioxide or chlorous acid in the final composition is less than about 50 ppm and the pH of the final composition is greater than 7.

8. The composition of claim 7 wherein the level of chlorine dioxide or chlorous acid in the final composition is less than about 25 ppm.

9. The composition of claim 8 wherein the level of chlorine dioxide or chlorous acid in the final composition is less than about 15 ppm.

10. The composition of claim 9 wherein the level of chlorine dioxide or chlorous acid in the final composition is less than about 10 ppm.

11. The composition according to claim 10 wherein the final composition is essentially free of chlorine dioxide or chlorous acid.

12. A method for the treatment or prevention of breath malodor, by administering to the oral cavity, an oral care lozenge composition according to claim 1.

13. A method for the treatment or prevention of breath malodor, by administering to the oral cavity, an oral care lozenge composition according to claim 7.

14. An oral care lozenge composition consisting essentially of:

(a) from about 0.1 mg to about 12 mg of chlorite ion; and (b) a pharmaceutically-acceptable lozenge oral carrier;

(c) from about 0.05% to about 0.3% fluoride ion;

wherein the level of chlorine dioxide or chlorous acid in the final composition is less than about 50 ppm and the pH of the final composition is greater than 7.

15. The composition of claim 14 wherein the level of chlorine dioxide or chlorous acid in the final composition is less than about 10 ppm.

16. An oral care lozenge composition consisting essentially of:

(a) a safe and effective amount of chlorite ion; and (b) a pharmaceutically-acceptable lozenge oral carrier comprising from about 0.5% to about 0.3% fluoride ion;

wherein the level of chlorine dioxide or chlorous acid in the final composition is less than about 50 ppm and the pH of the final composition is greater than pb 7.

* * * * *